(12) United States Patent
Zhang et al.

(10) Patent No.: US 7,195,790 B2
(45) Date of Patent: Mar. 27, 2007

(54) MODIFICATION OF CYCLOOXYGENASE AND LIPOXYGENASE ACTIVITY WITH ASTERIDAE EXTRACTS AND OPTIONALLY BOSWELLIC ACID

(75) Inventors: Peter X. Zhang, Castro Valley, CA (US); Michael T. Yatcilla, Oakland, CA (US)

(73) Assignee: Shaklee Corporation, Pleasanton, CA (US)

( * ) Notice: Subject to any disclaimer, the term of this patent is extended or adjusted under 35 U.S.C. 154(b) by 0 days.

(21) Appl. No.: 10/732,182

(22) Filed: Dec. 9, 2003

(65) Prior Publication Data

US 2004/0166182 A1    Aug. 26, 2004

Related U.S. Application Data

(60) Provisional application No. 60/507,655, filed on Sep. 30, 2003, provisional application No. 60/432,101, filed on Dec. 9, 2002.

(51) Int. Cl.
*A61K 36/00* (2006.01)
(52) U.S. Cl. ...................... 424/764; 424/725
(58) Field of Classification Search ............... 424/725, 424/778
See application file for complete search history.

(56) References Cited

U.S. PATENT DOCUMENTS

| | | | |
|---|---|---|---|
| 4,466,923 A * | 8/1984 | Friedrich ................. | 554/8 |
| 5,288,725 A | 2/1994 | Witherup et al. | |
| 5,968,519 A | 10/1999 | Youssefyeh et al. | |
| 5,972,993 A * | 10/1999 | Ptchelintsev ............. | 514/449 |
| 6,174,876 B1 | 1/2001 | Simmet et al. | |
| 6,245,340 B1 | 6/2001 | Youssefyeh | |
| 6,264,995 B1 | 7/2001 | Newmark et al. | |
| 6,534,086 B1 | 3/2003 | Krumhar | |
| 6,541,045 B1 | 4/2003 | Charters et al. | |
| 6,746,695 B1 * | 6/2004 | Martin et al. ............. | 424/734 |
| 2001/0024664 A1 | 9/2001 | Obukowicz et al. | |
| 2004/0073060 A1 * | 4/2004 | Gokaraju et al. ........ | 562/498 |

FOREIGN PATENT DOCUMENTS

| EP | 0755940 | 1/1997 |
|---|---|---|
| JP | 2000014354 | 1/2000 |

OTHER PUBLICATIONS

Akihisa et al.; "Triterpene Alcohols from the Flowers of Compositae and their Anti-inflammatory Effects"; Phytochemistry, vol. 43, No. 6, pp. 1255-1260, 1996.*

Ammon, H., *Boswellic Acids (Components of Frankincense) as the Active Principle in Treatment of Chronic Inflammatory Diseases*, Wien Med Wochenschr., 152(15-16):373-8 (2002) (Abstract).

Cassileth and Yeung, *Boswellia*, Brainlife Brain Tumor Medical Database, 3 pp. (last updated Jan. 13, 2003) <http://www.brainlife.org/education/integrative/supplements/boswellia/cassileth_boswellia.htm>.

Hong et al., *Inhibitory Effect of a Korean Traditional Medicine, Honghwain-Jahage (Water Extracts of Carthamus tinctorius L. Seed and Hominis placenta) on Interleukin-1-Mediated Bone Resorption*, J. Ethnopharmacol., 79(2):143-148 (2002) (Abstract).

Kee Chang Huang, The Pharmacology of Chinese Herbs, 318-320 ($2^{th}$ ed. 1999).

Kimmatkar et al., *Efficacy and Tolerability of Boswellia serrata Extract in Treatment of Osteoarthritis of Knee—A Randomized Double Blind Placebo Controlled Trial*, Phytomedicine, 10(1):3-7 (2003).

Li and Che, *Studies on Chemical Components of Carthamus tinctorius petals*, Yao Xue Xue Bao, 33(8):626-8 (1998) (Abstract).

Lin et al., *Anti-Inflammatory and Radical Scavenge Effects of Arctium lappa*, Am. J. Chin. Med., 24(2):127-37 (1996) (Abstract).

Ruppelt et al., *Pharmacological Screening of Plants Recommended by Folk Medicine as Anti-Snake Venom—I. Analgesic and Anti-Inflammatory Activities*, Mem. Inst. Oswaldo Cruz, 86(2):203-5 (1991) (Abstract).

Safayhi et al., *Boswellic Acids: Novel, Specific, Nonredox Inhibitors of 5-Lipoxygenase*, J. Pharmacol. and Exper. Ther., 261(3):1143-1146 (1992).

Singh et al., *Pharmacology of an Extract of Salai Guggal ex-Boswellia Serrata, a new Non-Steroidal Anti-Inflammatory Agent*, Agents Actions, 18(3-4):407-12 (1986) (Abstract).

Yuk, et al., *Inhibitory Effect of Carthamus tinctoris L. Seed Extracts on Bone Resorption Mediated by Tyrosine Kinase, COX-2 (Cyclooxygenase) and PG (Prostaglandin) E2*, Am. J. Chin. Med., 30(1):95-108 (2002) (Abstract).

* cited by examiner

*Primary Examiner*—Christopher Tate
*Assistant Examiner*—S. B. McCormick-Ewoldt
(74) *Attorney, Agent, or Firm*—Klarquist Sparkman, LLP

(57) ABSTRACT

Extracts from plants in the Asteridae subfamily, such as *Carthamus tinctorious*, are effective to selectively inhibit COX-2 activity and/or enhance COX-1 activity. When Asteridae extracts are combined with boswellic acid, the combination exhibits a synergistic inhibitory effect on both COX-2 and LO. Such extracts and combinations are used in methods of selectively inhibiting COX-2, inhibiting LO, and/or enhancing COX-1 activity as well as in the methods of treating conditions that would respond favorably to any of these effects.

22 Claims, 3 Drawing Sheets

Simplified Process Flow Diagram

Fig. 2 *Carthamus Tinctorius* Extract Inhibition of COX-2

Fig. 3 *Carthamus tinctorius* Extract Enhancement f COX-1 activity
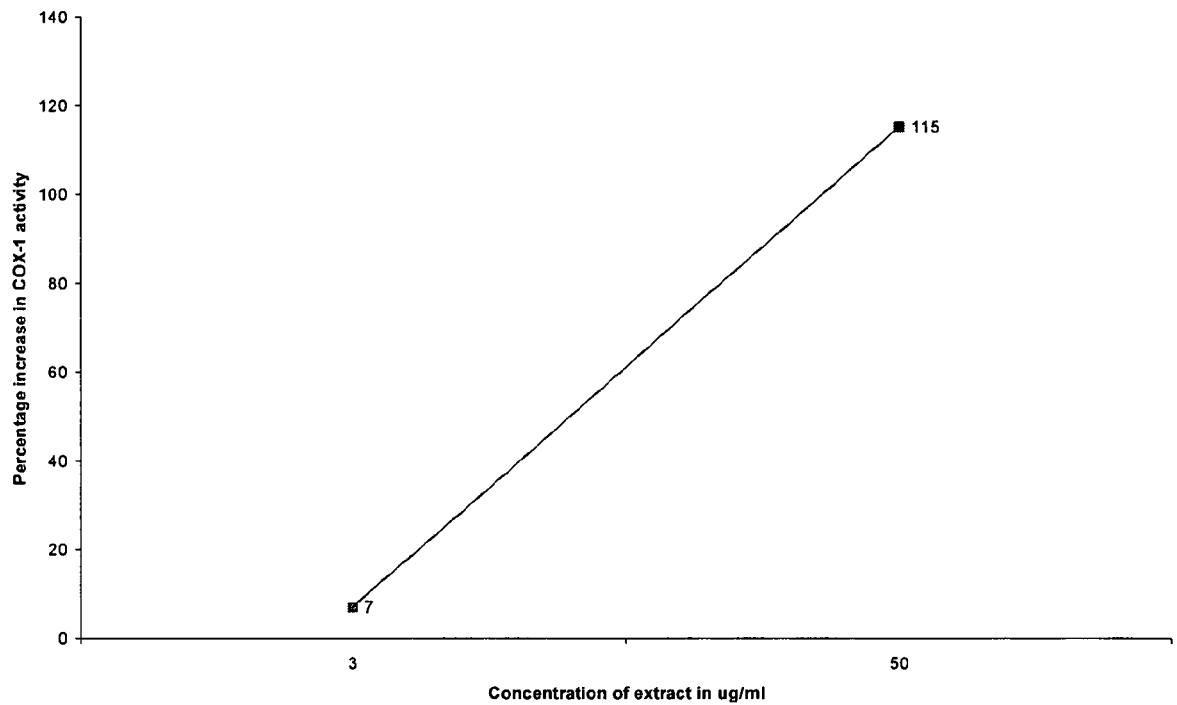
Fig. 4 Inhibition of COX-2 by extracts of C. tinctorious, B. serrata, and a combination thereof
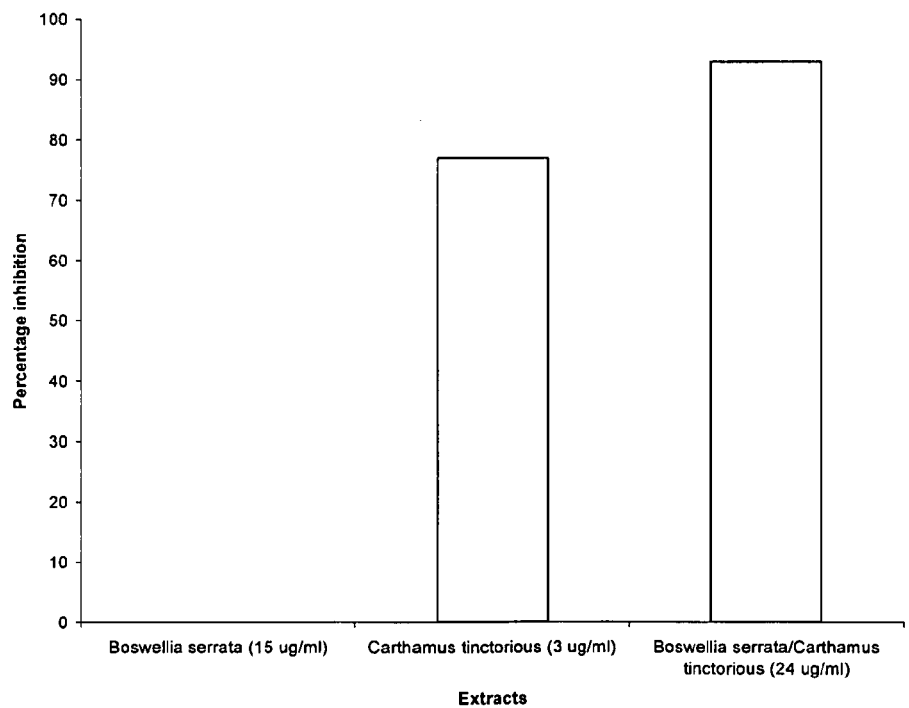

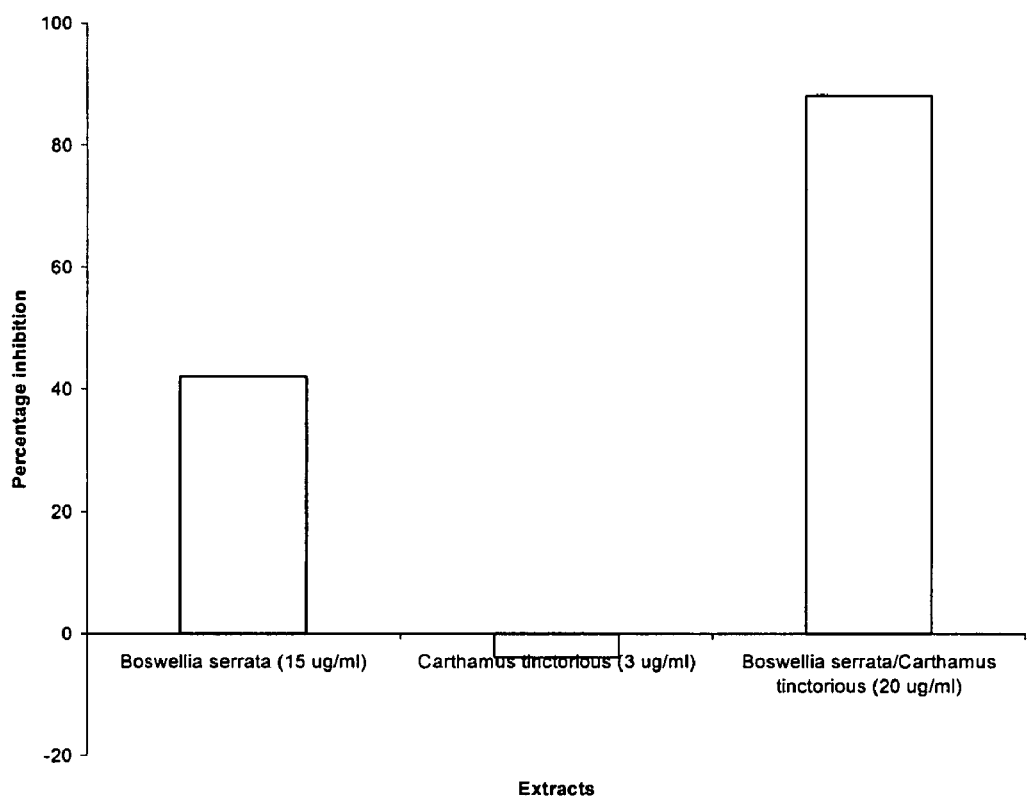
Fig. 5 Inhibition of 5-LO by xtracts of C. tinct rious, B. serrata, and a combination thereof

MODIFICATION OF CYCLOOXYGENASE AND LIPOXYGENASE ACTIVITY WITH ASTERIDAE EXTRACTS AND OPTIONALLY BOSWELLIC ACID

CROSS REFERENCE TO RELATED APPLICATION

This disclosure claims priority to U.S. Provisional Application No. 60/432,101, filed Dec. 9, 2002, and to U.S. Provisional Application No. 60/507,655, filed Sep. 30, 2003, which are both incorporated by reference herein.

FIELD

The extracts, compositions, and methods disclosed herein relate to pharmaceutical/nutraceutical extracts and compositions useful to reduce inflammation and to treat inflammation related conditions.

BACKGROUND

Prostaglandins (PG) and leukotrienes (LT) play a critical role in pathophysiology. In particular, inflammation is both initiated and maintained by the overproduction of prostaglandins and leukotrienes in injured cells. Prostaglandins and leukotrienes are biosynthesized on demand from arachidonic acid, a 20-carbon fatty acid that is derived from the breakdown of cell-membrane phospholipids. Prostaglandins and leukotrienes are produced via separate enzyme pathways known as the cyclooxygenase (COX) and lipoxygenase (LO) pathways, respectively.

The first step in the synthesis of prostaglandins is the cyclooxygenase reaction. An enzyme, cyclooxygenase (COX) (also known as prostaglandin H synthase (PGHS)) catalyzes the conversion of arachidonic acid into the endoperoxide $PGG_2$, and endoperoxide $PGG_2$ to $PGH_2$. $PGH_2$ is in turn metabolized by one or more prostaglandin synthase ($PGE_2$ synthase, $PGD_2$ synthase, etc.) to generate the final "2-series" prostaglandins, such as $PGE_2$, $PGD_2$, $PGF_{2a}$, $PGI_2$, and others, as well as thromboxanes and prostacyclins.

As disclosed in U.S. Pat. No. 6,048,850 (to Young et al.), there are two forms of COX. Cyclooxygenase-1 (COX-1) is "constitutively" expressed in most tissues. It is described as a "housekeeping" enzyme, regulating normal cellular processes, such as gastric cytoprotection, vascular homeostasis, platelet aggregation, and kidney function. Although generally described as "constitutive," COX-1 also can be induced. Ferraz et al., *Gastroenterology*, 113(1):195–204 (1997). Further, an increase in COX-1 mediated prostaglandin synthesis, such as $PGI_2$, has been reported as important in preventing gastric lesion formation. Harada et al., *J. Lab. Clin. Med.*, 129(6):620–6 (1997). This may be because prostaglandins help maintain an intact gastric mucosal barrier by increasing secretion of mucus and bicarbonate, maintaining mucosal blood flow, and decreasing acid secretion. Fuller and McKenzie, *U.S. Pharmacist*, 17:35–36, 41–42, 47–48, 53–55, 87 (1992).

Cyclooxygenase-2 (COX-2) is usually undetectable in most tissues; however, its expression is increased during states of inflammation or, experimentally, in response to mitogenic stimuli. COX-2 is accordingly referred to as "inducible." It is this inducible COX-2 form that is responsible for prostaglandin overproduction through the COX pathway in response to tissue injury, and stimulation by growth factors and proinflamatory cytokines.

As the COX pathway is the rate-limiting step for prostaglandin synthesis, the COX reaction is the principal target for anti-inflammatory drug action. And it is inhibition of COX activity that accounts for the activity of the non-steroidal anti-inflammatory drugs (NSAIDs), such as aspirin, acetaminophen, ibuprofen, naproxen, indomethacin. These drugs however, are nonselective in their inhibition of COX. Thus, they inhibit the activity of COX-2 in inflammation, which produces a desirable therapeutic effect. But they also inhibit the activity of COX-1 in non-inflamed cells, which interferes with the normal production of prostaglandins necessary for normal physiological functions. COX-1 activity generates protective gastric mucosal prostaglandins, as disclosed in U.S. Pat. No. 6,344,323 (Siefert). Inhibiting such prostaglandin production by COX-1 can produce undesirable side effects, such as renal failure, and gastrointestinal mucosal disorders, for example, gastritis, gastrointestinal bleeding, and ulcers. An estimated 16,500 deaths each year result from gastrointestinal bleeding associated with traditional NSAIDs, as reported by Moskowitz, *Consultant*, 40:1370 (2000).

In an effort to utilize the benefits of COX-2 inhibition without the side effects of COX-1 inhibition, pharmaceutical compounds have been developed to selectively inhibit the activity of COX-2. For example, celecoxib (marketed by Pharmacia/Pfizer as CELEBREX) and rofecoxib (marketed by Merck as VIOXX) are both selective COX-2 inhibitors. Nimesulide is a Cox-2 inhibitor marketed under the trade name MESULID in Europe. COX-2 selectivity can be quantified by calculating the COX-2/COX-1 $IC_{50}$ (inhibitor concentration at which 50% inhibition occurs) ratio. Compounds with a ratio less than one can be considered relatively COX-2 selective—the lower the ratio, the higher the COX-2 selectivity.

The literature is replete with reports that selective COX-2 inhibiting compounds are usefull in treating a variety of conditions, which are mediated at least in part by inflammation. For example, COX-2 inhibitors have been reported as useful to treat conditions such as general pain, osteoarthritis and rheumatoid arthritis, Whelton et al., *Am J. Ther*, 7(3): 159–75 (2000), menstrual pain associated with primary dysmenorrhea, Daniels et al., *Obstet Gynecol*, 100(2):350–8 (2002), cancers, such as colon cancer, Nagatsuka, et al., *Int'l. J. Cancer*, 100(5):515–9 (2002), oral cancer, Wang et al., *Laryngoscope*, 112(5):839–43 (2002), and skin cancer, Lee et al., *Anticancer Res.*, 22(4):2089–96 (2002); Fischer, *J. Environ. Pathol. Toxicol. Oncol.* 21(2):183–91 ((2002), and Alzheimer's disease, Aisen, *J. Pain Symptom Manage.*, 23(4 Suppl):S35–40 (2002).

The herb *Carthamus tinctorious* (safflower) is a member of the family Compositae and the sub-family Asteridae, which includes the sunflower, artichoke, tarragon, southernwood, and many ornamentals. *Carthamus tinctorious* flower petals have traditionally been used in Chinese medicine to improve blood circulation and to treat pain or inflammation. Kee Chang Huang, PHARMACOLOGY OF CHINESE HERBS, $2^{nd}$ Ed., p.318–20 (1999). Extracts of *Carthamus tinctorious* flowers have been made, for example a 60% ethanol/40% water extract, and investigated to determine chemical constituents of the plant, such as flavanoids, as well as to determine blood circulation effects caused by the extracts. Li & Che, *Yao Xue Xue Bao*, 33:626–8 (1998). A composition comprising *Echinacea purpourea* and one or more of several other plants including *Carthamus tinctorious* has been disclosed as an inhibitor of $PGE_2$ production in Japanese Patent Application No. 10184282 by Yumiko et al. However, no references are known that disclose that any extract of *Carthamus tinctorious*, or any other extract from a plant in the Asteridae sub-family, selectively inhibits COX-2 activity. Also, although pharmaceutical compositions of extracts of the seeds of *Carthamus tinctorious* have been disclosed for the treatment of inflammation, U.S. Pat. No. 6,245,340 (to Youssefyeh), no pharmaceutical compositions including extracts from the flower or other parts of *Carthamus tinctorious* other than the seeds are known.

In the lipoxygenase pathway, lipoxygenase (such as 5-LO) converts arachidonic acid into a hydroperoxy eicosatetraenoic acid (such as 5-hydroperoxy-eicosatetraenoic acid (5-HPETE)), which is converted to the leukotriene LTA4 that can in turn be converted to leukotrienes $LTB_4$, $LTC_4$, or $LTD_4$. Leukotrienes are implicated in many inflammatory diseases and related conditions including cancer proliferation and also can contribute to the development of gastrointestinal ulcers by contributing to the inflammatory process. Leval et al., *Curr. Med. Chem.*, 9:941–62 (2002); Fiotucci et al., *Biochem Pharmacol.*, 62:1433–8 (2001).

Because of the inflammatory action of leukotriene production, inhibitors of lipoxygenase have been used to inhibit the production of leukotrienes in order to inhibit inflammation. Muller-Peddinghaus, *Physiol Pharmacol.*, 48:529–36 (1997).

The plant *Bosswellia serrata* (specifically the gum resin of the plant) has been used for the treatment of rheumatoid arthritis and gout by the practitioners of Ayurvedic medicines in the Indian system of medicine, as discussed in EP-A 7559000040. In particular, various extracts of the gum resin containing acids known as boswellic acids have shown anti-inflammatory and anti-arthritic activity in laboratory animals, as well as during clinical trials. Atal et al., *Ind. J. Pharm*, 12, 59 (1980); Pachnanda et al., *Ind. J. Pharm*, 13, 63 (1981). Singh et al., established that an alcohol extract of *Boswellia serrata* gum resin displayed anti-inflammatory activity in carrageenan induced edema in rats and mice and dextran induced edema in rats. Singh et al., *Agent and Action*, 18:407 (1986). Safayhi et al. showed that an ethanolic extract of *Bosswellia serrata* inhibited 5-LO product formation. Safayhi et al, *Planta Med.*, 66:110–3 (2000).

The effect of *Bosswellia serrata* extract on COX-2 activity has been studied, but boswellic acids isolated from the gum resin of *Bosswellia serrata* were found not to inhibit COX-2 activity. Ammon et al., *J. Ethnopharmacol.* 38:113–9 (1993); Safayhi et al., *J. Pharmacol. Exp. Ther.*, 261:1143–6 (1992).

SUMMARY

It has now been discovered that an Asteridae extract, such as an extract from a plant of the *Carthamus* genera, for example, *Carthamus tinctorious*, exhibits selective COX-2 inhibition and/or enhancement of COX-1 activity. It has further been discovered that the novel combination of an Asteridae extract and boswellic acid selectively inhibits COX-2 activity and also inhibits LO activity. Further, this combination inhibits both COX-2 and LO to an unexpectedly superior degree than either component of the combination alone. In particular, COX-2 activity is inhibited by this combination to a greater degree than COX-2 is inhibited by an Asteridae extract alone. This is surprising because, as discussed above, boswellic acid alone does not inhibit COX-2 activity. Also, the combination inhibits LO activity more than boswellic acid alone. This is surprising because Asteridae extract alone does not inhibit LO activity. Such synergistic activity is advantageous in some cases because a lesser amount of each Asteridae extract and boswellic acid is required to achieve the same COX-2 and/or LO inhibition than if each extract were used separately.

Accordingly, Asteridae extracts, such as *Carthamus tinctorious* extract, are useful for modifying COX activity by selectively inhibiting COX-2 activity and/or enhancing COX-1 activity. Moreover, such extracts are useful for treating any conditions that would respond favorably to the inhibition of COX-2 and/or enhancement of COX-1 activity. Such extracts also are useful for countering COX-1 inhibition caused by other agents, such as NSAIDs that inhibit COX-1 activity. Further, combinations of an Asteridae extract and boswellic acid are useful for modifying COX and LO activity by selectively inhibiting COX-2 activity, inhibiting LO activity, and/or enhancing COX-1 activity. Moreover, such combinations are useful for treating any conditions that would respond favorably to the inhibition of COX-2 and/or inhibition of LO activity and/or the enhancement of COX-1 activity.

Disclosed herein are therapuetic agents including Asteridae extracts that are effective to selectively inhibit COX-2 and/or enhance COX-1 activity. In some cases the disclosed therapeutic agents further include boswellic acid, such as from an extract from a plant from the family Burseraceae, such as a plant from the genus *Boswellia*, for example *Bosswellia serrata*, and are further effective to inhibit LO activity.

Also disclosed are methods of administering the disclosed therapeutic agents and combinations of Asteridae extracts and boswellic acid to subjects to selectively inhibit COX-2 activity and/or to increase COX-1 activity and/or inhibit LO activity. These disclosed methods are used to treat conditions that would respond favorably either to inhibition of COX-2 and/or LO activity and/or enhancement of COX-1 activity, such as pain, inflammation, arthritis, cancer, Alzheimer's disease, renal failure, and gastrointestinal mucosal disorders and injury, for example, gastritis, gastrointestinal perforation, gastrointestinal bleeding, and ulcers. Additionally such methods are used prophalactically with subjects at demonstrated risk for conditions such as the conditions described above to prevent, inhibit, or reduce such conditions or reduce associated injury or discomfort.

BRIEF DESCRIPTION OF THE DRAWINGS

FIG. 2 is a graph of the percentage of COX-2 inhibition for different concentrations (in μg/ml) of a crude 6.5:1 methanol *Carthamus tinctorious* extract.

FIG. 3 is a graph of the percentage increase in COX-1 activity for different concentrations (in μg/ml) of a crude 6.5:1 methanol *Carthamus tinctorious* extract.

FIG. 4 is a graph of the percentage of COX-2 inhibition caused by a *Boswellia serrata* extract at 15 μg/ml, *Carthamus tinctorious* extract at 3 μg/ml, and an about 1000:150 combination of the *Bosswellia serrata* extract and the *Carthamus tinctorious* extract, respectively, at about 24 μg/ml.

FIG. 5 is a graph of the percentage of 5-LO inhibition caused by a *Boswellia serrata* extract at 15 μg/ml, *Carthamus tinctorious* extract at 3 μg/ml, and an about 1000:150 combination of the *Bosswellia serrata* extract and the *Carthamus tinctorious* extract, respectively, at about 20 μg/ml.

DETAILED DESCRIPTION

Terms

Figure 1:
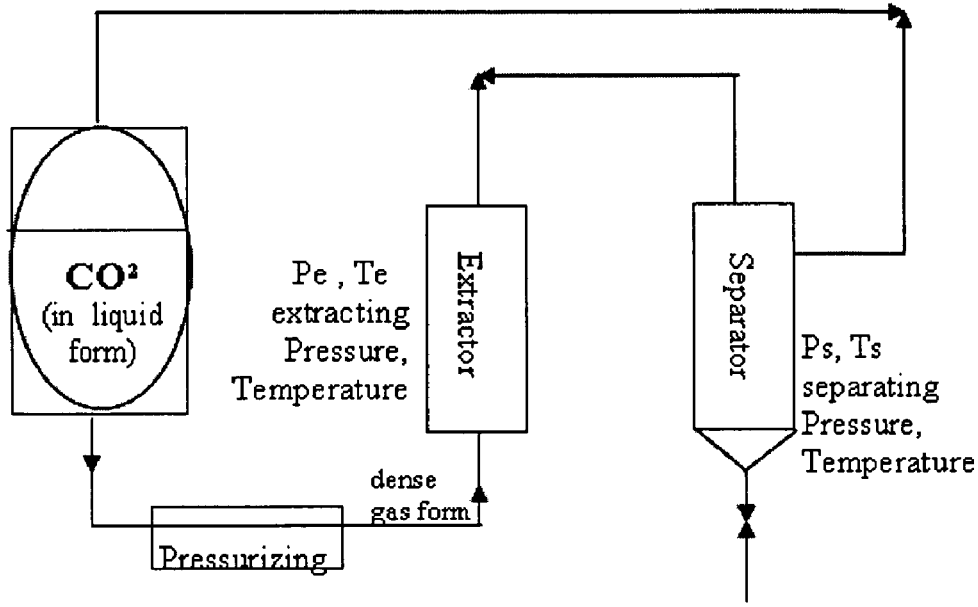
FIG. 1 is a schematic of a supercritical extraction process.
Figure 1:
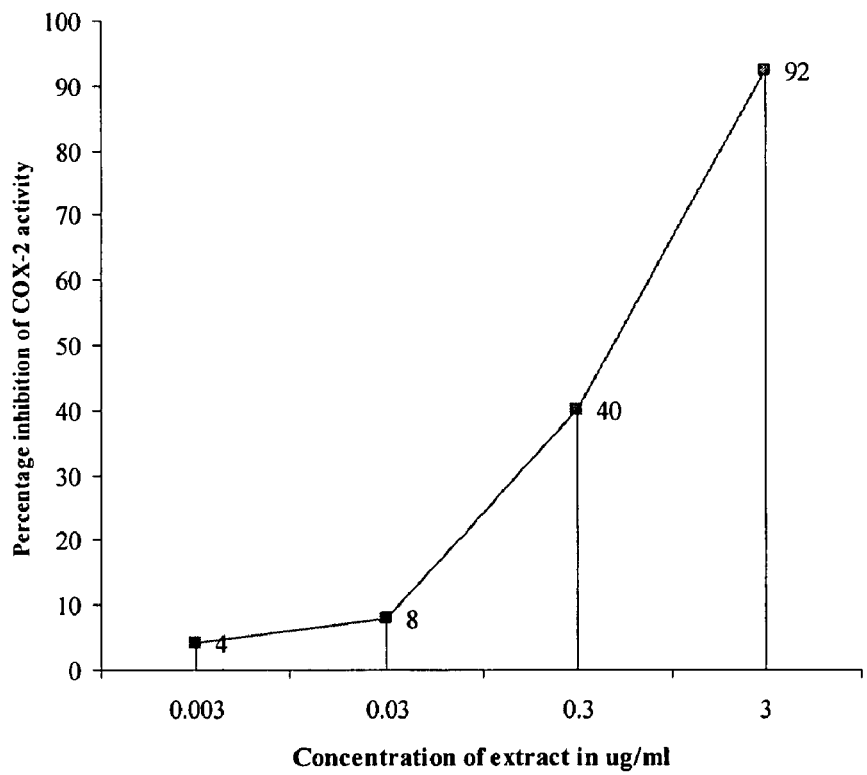

The term "subject" means an animal, such as a mammal, for example a human.

The term "extract" refers to a concentrate of soluble plant components obtained by means of a solvent (including a mixture of solvents) from a plant (or portions thereof), optionally under pressure, ultrasonic, or at a particular temperature or range of temperatures. Suitable solvents include water, organic solvents, and supercritical fluids. Those of ordinary skill in the art are knowledgeable concerning many methods of producing a plant extract. Suitable techniques are described in U.S. Pat. Nos., 5,891,440, 5,874,084, and 5,908,628. A typical method of making an extract includes grinding up plant material (for example the flowers of a plant) with a grinding device, such as a mortar and pestle, placing the plant material into a container, adding a solvent to the container, allowing the plant material and solvent to sit for a period of time, such as overnight, filtering the plant material from the solvent, and then evaporating the solvent to leave an extract, for example by heating the plant/solvent mixture to a particular temperature, such as about 35–45° C., optionally under vacuum, such as about negative 500 to about negative 1000 bar. An extract that has not been fractionated after the initial extraction is known as a crude extract. An extract that has been fractionated from the crude extract is known as a purified extract. Herein, the term extract is used in general to refer to crude extracts, fractions of extracts, and otherwise purified extracts.

A "fraction" of an extract is a portion of an extract that has been extracted from the extract based on a common property of the fraction that distinguishes it from the remainder of the extract. Fractionating includes, for example, solvent/solvent partitioning (Kupchan method), in which a crude extract is disolved or suspended with water or any other solvent, then partitioned or any other suitable solvent (as will depend on the solvent used for suspension), such as ethyl acetate, chlorform, and butanol. For example, in some cases, an ethanol extract is suspended in water and partitioned with ethyl acetate. The two solvents form separate layers which are separated into fractions and evaporated to form purified extracts. In other cases fractionating includes solid-phase separation, for example by column chromatography. In column chromatography an extract is loaded onto a solid phase, such as silicone, packed in a column. A solvent, such as ethanol, is run through the column, collected, and evaporated to obtain a fraction of the extract. In some cases, a series of different solvents are run through the column to obtain numerous fractions. Some solvents in the series can be used to wash out untargeted components. For example, if the desired components are soluble in organic solvents, a water solvent can be used to extract untargetted components so that subsequent organic solvents include higher concentrations of targetted components.

The term "plant:extract ratio" refers to the amount of extract resulting from the extraction process. For example, if 10 grams of plant material is extracted to 1 gram of extract (after solvent evaporation), the plant:extract ratio is 10:1. Often the ratio will simply be noted before the solvent is used for extraction, for example, if 10 grams of plant material is extracted to 1 gram of extract with methanol, the extract may be refered to as a 10:1 methanol extract.

The term "organic solvent" refers to solvents including organic compounds, such as alcohols, for example methanol, ethanol, propanol and butanol, polyols such as propylene glycol, 1,3-butylene glycol and glycerin, and other organic solvents, such as acetone, ethyl acetate, hexane, hexene, chlorform, acetonitrile, acetic acid, and mixtures thereof. An organic solvent includes a solvent that is part organic solvent and part water, for example a solvent that is part ethanol (such as from 20–99%) and part water (such as from 1–80%) (% w/w).

The term "organic solvent extract" refers to an extract extracted by an organic solvent.

The term "supercritical extract" refers to an extract extracted using a supercritical fluid as a solvent, for example as described in U.S. Pat. Nos., 5,932,101 and 5,120,558. An advantage of supercritical extraction in some cases is that there is no solvent residue in the extract. In particular cases the plant or a portion thereof is extracted with supercritical fluid carbon dioxide. When carbon dioxide gas ($CO_2$) is compressed above about 73 bar at a temperature above about 31° C. it transforms into a dense gas/fluid known as supercritical $CO_2$. Supercritical $CO_2$ is biologically compatible and generally regarded as safe (GRAS) by the FDA.

A typical supercritical fluid extraction, such as with supercritical $CO_2$, includes placing plant material in a sealed extractor vessel pressurized to a pressure of about 73 bar or higher (such as from about 200–700 bar) and heated to a temperature of about 31° C. or higher (such as about 35–60° C.), pumping supercritical fluid $CO_2$ into the extractor and through the plant material to solvate the soluble portions of the plant material until a specific raw material/carbon dioxide ratio is achieved, for example about 1:8, pumping the supercritical $CO_2$ into a separate separator vessel, and relieving the pressure in the separator to allow the $CO_2$ to return to its gaseous form and extract to be separated from the $CO_2$ solvent. Fractions of the extract can be obtained by relieving the pressure in the separator vessel incrementally and removing the extract obtained at each increment or by passing the loaded supercritical fluid through a series of separators at successively lower pressures and temperatures. A schematic of a supercritical $CO_2$ extraction process is illustrated in FIG. 1.

The term "Asteridae extract" refers to an extract (or mixture of extracts) from a plant (or plants) from the sub-family Asteridae of the family of plants known as Compositae, for example plants from the genus *Arctium, Carthamus*, for example, *Carthamus tinctorius* (safflower), *Centaurea, Cnicus, Crepis, Cynara*, for example, *Cynara scolymus* (globe artichoke), *Dimorphotheca, Forsythia, Haplopappus, Helianthus*, for example, *Helianthus annulus* (sunflower), *Saussurea*, and *Trachelospermum*.

"Organic solvent/supercritical Asteridae extract" (OSSC Asteridae extract) refers to an Asteridae extract that was extracted with an organic solvent or a supercritical fluid solvent.

"Water Asteridae extract" refers to an Asteridae extract that was extracted with water.

Boswellic acid refers to at least one of the tetracyclic or pentacyclic triterpenic acids that can be found in plants from the family Burseracea, such as from the genera *Boswellia, Commiphora*, and *Bursera*, for example *Boswellia* (*serrata, papyrifera, cartei, thurifera, glabra, bhaw-dajiana, oblongata*, and *socotrana*), as well as biologically acceptable forms of such acids, including biologically acceptable salts of such acids. Exemplary boswellic acids include β-boswellic acids, such as β-boswellic acid, acetyl-β-boswellic acid, acetyl-11-keto-β-boswellic acid (for example 3—O-acetyl-11-keto-β-boswellic acid), and 11-keto-β-boswellic acid as well as 3α-tirucall-8,24-dien-21-oic acid, 3-ketotirucall-8,24-dien-21-oic acid, 3-α-hydroxytirucall-8,24-dien-21-oic acid, 3 β-hydroxy tirucall-8,24-dien-21-oic acid.

Boswellic acids can be provided in purified form, for example as an isolated boswellic acid, such as 3-O-acetyl-11-keto-β-boswellic acid, or in a mixture of isolated boswellic acids, for example a mixture of β-boswellic acid, acetyl-β-boswellic acid, acetyl-11-keto-β-boswellic acid (such as 3-O-acetyl-11-keto-β-boswellic acid), and 11-keto-β-boswellic acid, or as part of a plant extract including at least one boswellic acid, for example an alcohol extract from a plant of genera *Boswellia* including acetyl-11-keto-β-boswellic acid (such as 3-O-acetyl-11-keto-β-boswellic acid). The chemical structures shown below illustrate some exemplary boswellic acids, namely, β-boswellic acid (I), acetyl-β-boswellic acid (II), 11-keto-β-boswellic acid (III), acetyl-11-keto-β-boswellic acid (IV), β-boswellic acid (V), β-boswellic acid (VI), 3 α-tirucall-8,24-dien-21-oic acid (VII), 3-ketotirucall-8,24-dien-21-oic acid (VIII), 3 α-hydroxytirucall-8,24-dien-21-oic acid (IX), 3 β-hydroxy tirucall-8,24-dien-21-oic acid (X):

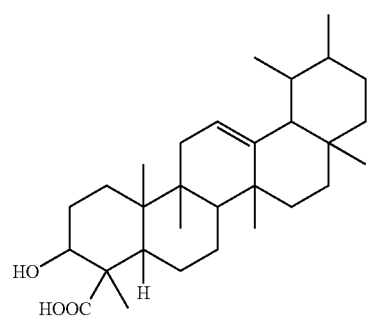

(I)

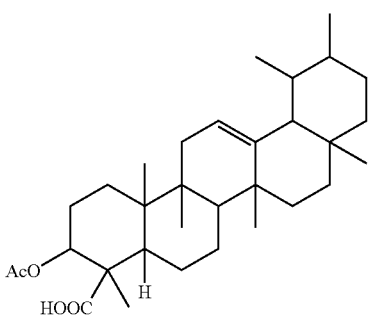

(II)

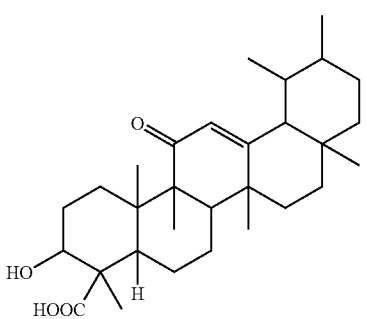

(III)

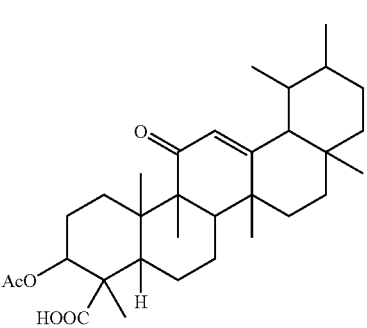

(IV)

-continued

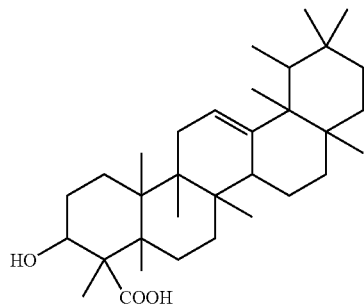

(V)

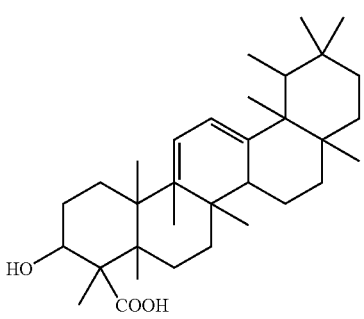

(VI)

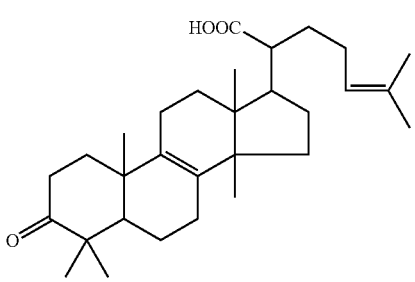

(VII)

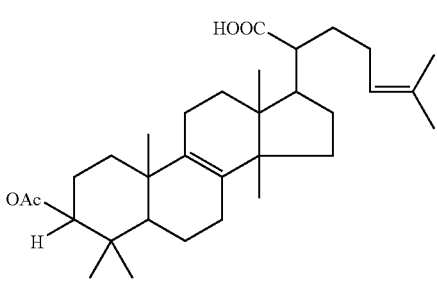

(VIII)

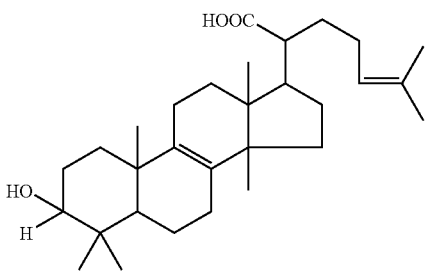

(IX)

-continued

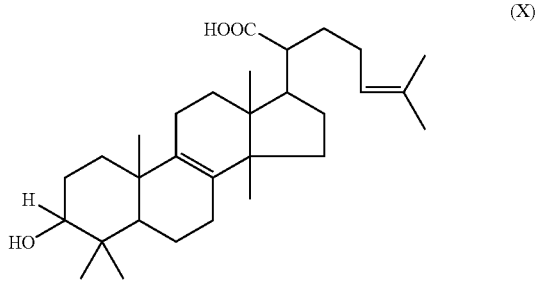

(X)

The term "Burseracea extract" refers to an extract or extracts from a plant of from the family Burseracea that includes boswellic acid, such as an extract from the genera *Boswellia, Commiphora,* and *Bursera,* for example *Boswellia* (*serrata, papyrifera, cartei, thurifera, glabra, bhaw-dajiana, oblongata,* and *socotrana*).

"Treating" a condition refers to reversing, alleviating, inhibiting the progress of, or preventing the condition or one or more symptoms or signs of the condition.

A "therapeutically effective amount" of an Asteridae extract or a combination of Asteridae extract/boswellic acid is an amount effective to treat a particular condition or a symptom or sign of the condition.

A "COX-2/LO mediated condition" is any condition that responds favorably to COX-2 and/or or LO inhibition.

A "condition for which COX-1 inhibition is disadvantageous" includes any condition that is mediated or exacerbated by COX-1 inhibition.

A "condition for which COX-1 enhancement is favorable" includes any condition that responds favorably to COX-1 enhancement, for example a condition that is inhibited, reduced, or prevented by COX-1 enhancement, such as a condition mediated or exacerbated by COX-1 inhibition.

A "pharmaceutical composition" refers to a composition including the disclosed therapeutic agent(s) and a pharmaceutically acceptable carrier.

"Selective COX-2 inhibition" and "selectively inhibiting COX-2" refer to inhibiting COX-2 to a greater degree than COX-1, for example where the COX-2/COX-1 $IC_{50}$ ratio of a substance is less than 1.

Therapeutic Agents

The disclosed therapeutic agents include an Asteridae extract in an amount effective to selectively inhibit COX-2 and/or enhance COX-1 activity. The Asteridae extract is an extract from the whole plant or from portions of the plant, such as the flower, stem, root, and/or seeds. In specific cases, the Asteridae extract is an extract from the flower of such a plant. In certain cases the Asteridae extract is an extract from any portion of the plant other than the seeds. In particular cases the Asteridae extract is an extract from a plant in the genus *Arctium, Carthamus,* for example, *Carthamus tinctorius* (safflower), *Centaurea, Cnicus, Crepis, Cynara,* for example, *Cynara scolymus* (globe artichoke), *Dimorphotheca, Forsythia, Haplopappus, Helianthus,* for example, *Helianthus annulus* (sunflower), *Saussurea,* and *Trachelospermum*. In specific cases the Asteridae extract is an extract from a plant in the genus *Carthamus,* such as *Carthamus tinctorious*. In certain embodiments, the Asteridae extract is an OSSC Asteridae extract, a water Asteridae extract, or a mixture thereof.

Any organic solvent can be used to make an OSSC Asteridae extract that is either safe for consumption by a subject or that is removed subsequent to extraction and prior to administration to a subject. In particular cases the organic solvent used for extraction includes an alcohol, such as methanol or ethanol, acetonitrile, acetone, ethyl acetate, hexene and/or mixtures thereof.

Any supercritical fluid can be used to make an OSSC Asteridae extract. In particular cases, supercritical fluid $CO_2$ is used to make an OSSC Asteridae extract.

In some cases the Asteridae extract, such as an OSSC Asteridae extract, is an extract that was extracted at or below a particular temperature, for example with a solvent temperature at or below about 60° C., such as from about 0° C. to about 60° C., for example from about 0° C. to about 50° C. or about 0° C. to about 35° C., and an evaporation temperature at or below about 60° C., such as from about 20° C. to about 60° C., for example from about 30° C. to about 50° C. or about 35° C. to about 45° C. In certain cases, extraction at temperatures above about 60° C., for example 65° C. or above, can impair the COX-2 inhibition of the OSSC Asteridae extract relative to extracts prepared at lower temperatures or even cause the extract to not inhibit COX-2.

In some cases the Asteridae extract is freeze-dried, such as at about −50° C. to about −80 °C. to remove liquid from the extract to increase the storability of the extract and adapt the extract for easy incoporation into unit doses, for example by powdering the freeze-dried extract. In certain cases the extract is too oily for effective freeze drying. An oil adsorbent such as silicon dioxide or corn starch, for example cyclodextrin or schardinger dextrin, is added in some cases, such as to a crude ethanol extract, to increase the effectiveness of freeze drying. For example, about 10% to about 50% (by weight) of corn starch is added to the extract before freeze drying in some cases.

The Asteridae extract is effective to selectively inhibit COX-2 and/or enhance COX-1 activity. In some cases the Asteridae extract is effective to selectively inhibit 50% or more of COX-2 activity, such as 70% or 80% or more of COX-2 activity, for example 90% of more of COX-2 activity. In some cases the selective COX-2 inhibiting Asteridae extract also either does not significantly inhihibit COX-1 activity or is effective to enhance COX-1 activity, such as enhancing COX-1 activity by about 1–300%, such as about 1–150% for example about 1–50% or 1–15%.

In some instances the Asteridae extract is fractionated to produce a purified extract. In some cases, fractionating is performed by solvent/solvent partitioning. For example, in some cases, an ethanol Asteridae extract is suspended in water and partioned with ethyl acetate. The water and ethyl acetate form separate layers which are separated into fractions and evaporated to form purified extracts. In other cases fractionating includes solid-phase separation, for example by column chromatography.

One of ordinary skill in the art would be able to detemine these and other methods for fractionating extracts.

Fractionating is employed in some instances to obtain a fraction of an extract with particular desired COX inhibition and/or enhancement properties. The effect of a particular fraction can be determined by suitable bioassaying procedures to determine the effect of the extract on COX-2 and/or COX-1. Useful bioassaying procedures are know to those of skill in the art, and are described, for example, in Riendeau, D., et al., *British Journal of Pharmacology*, 121:105–17 (1997), Riendeau, D., et al., *Can. J. Physiolo. Pharmacol.*, 75:1088–95 (1997), and Warner, J. D., et al., *Proc. NatL. Acad. Sci.*, U.S.A. 96:7563–68 (1999).

In some cases, fractions of Asteridae extracts exhibit relatively higher COX-2 inhibition or COX-1 enhancement as compared to the unfractionated extract. For example a methanol fraction of a freeze-dried about 9:1 ethanol extract of *Carthamus tinctorious* that included about 15% cornstarch, such that the effective plant:extract ratio was about 7.5:1, which was obtained by column chromatography using a 10×2.5 cm column packed with HP-20 and pre-equilibrated with an acetonitrile/water solution inhibited about 98% COX-2 activity at a concentration of about 3 μg/ml, while the ethanol extract inhibited only 77% COX-2 activity at the same concentration and the pure ethanol extract (before mixing with cornstarch) inhibited 88% of COX-2 activity. In another example the water fraction of a freeze-dried about 9:1 ethanol extract of *Carthamus tinctorious* that included about 50% cornstarch, such that the effective plant:extract ratio was about 4.5:1 enhanced COX-1 activity by about 3% at 10 μg/ml, while a crude water Asteridae extract enhanced COX-1 activity by about 1% at the same concentration.

In some instances a fraction exhibiting the desired therapuetic effect (such as COX-2 inhibition and/or COX-1 enhancement) is further fractionated. The resultant subfractions are bioassayed for therapuetic effects. Through the fractionating process, Asteridae extracts with high potency and desired therapeutic characteristics are produced. In certain instances extracts are fractionated to obtain an Asteridae extract that only enhances COX-1 activity and does not inhibit COX-2 activity. Also, in certain instances an extract is fractionated to obtain a Asteridae extract that only inhibits COX-2 activity and does not enhance COX-1 activity.

In some instances the Asteridae extract includes two or more Asteridae extracts. For example, in some cases the Asteridae extract includes at least one extract from more than one genera or species, for example from two, or three, or more genera or species. For example, in some cases the Asteridae extract includes extracts from the flower or other parts of plants from the *Carthamus* and/or *Cynara* genera. In more specific instances the Asteridae extract includes an extract from the flower of a *Carthamus tinctorius* (safflower) and an extract from the flower or other parts of a *Cynara scolymus* (globe artichoke). In other cases the Asteridae extract includes two or more fractions of an extract from a single species, for example two or more fractions of an extract from *Carthamus tinctorius*.

In certain instances where the Asteridae extract includes two or more Asteridae extracts, each of the two or more extracts in the Asteridae extract is effective to selectively inhibit COX-2, for example two or more OSSC Asteridae extracts, such as an ethanol and a methanol extract. In other cases each of the two or more extracts in the Asteridae extract is effective to enhance COX-1 activity, for example an OSSC Asteridae extract and a water Asteridae extract. In still other cases one extract is effective to selectively inhibit COX-2 and another extract is effective to enhance COX-1 activity or both extracts are effective to inhibit COX-2 and enhance COX-1 activity. For example, in a specific instance, the Asteridae extract includes one fraction of an extract from the flower of a *Carthamus tinctorius* that is effective to selectively inhibit COX-2 and another fraction of an extract from the flower of a *Carthamus tinctorius* that is effective to increase COX-1 activity.

In particular cases the Asteridae extract, such as an OSSC Asteridae extract, includes one or more of the chemical compounds mataresinol monoglucoside, hydroxyarctiin (such as 2-hydroxyarctiin), linolinic acid, linoleic acid, and derivitives thereof. In particular cases the Asteridae extract contains at least about 0.001% of mataresinol monoglucoside, and/or hydroxyarctiin, for example from about 0.01% to about 2%. In particular cases the Asteridae extract contains at least about 0.001% of linoleic acid and/or linolinic acid, such as about 0.5 to about 5%, for example about 2%. Plants in the genera *Arctium, Carthamus, Centaurea, Cnicus, Crepis, Cynara, Dimorphotheca, Forsythia, Haploppus, Helianthus, Saussurea,* and *Trachelospermum* contain one or more of these compounds and/or deriviates of such compounds.

In some cases the disclosed therapeutic agent is a composition that includes Asteridae extract and further includes boswellic acid and is effective not only to inhibit COX-2 activity and/or enhance COX-1 activity, but also is effective to inhibit LO activity. This composition includes Asteridae extract and boswellic acid in any ratio. However, in certain cases the therapeutic agent includes about 50% to about 95% boswellic acid and about 5% to about 50% Asteridae extract (by weight).

The Asteridae extract includes any Asteridae extract disclosed above. In particular cases the Asteridae extract is an OSSC Asteridae extract, a water Asteridae extract, or mixtures thereof. In some cases the Asteridae extract is extracted at or below about 60° C.

The boswellic acid includes any boswellic acid or mixtures of boswellic acids, including mixtures of salts or other pharmaceutically acceptable forms of boswellic acid. In particular cases the boswellic acid includes β-boswellic acid, such as 3-O-acetyl-11-keto-β-boswellic acid, or other β-boswellic acids, or mixtures thereof. In some cases the boswellic acid is a Burseracea extract, such as a *Bosswellia serrata* extract. In particular cases the Burseracea extract includes about 40% to about 90% boswellic acids (by weight), for example about 50–80% boswellic acid, or about 60–70% boswellic acid. In specific cases the boswellic acids in the Burseracea extract include about 5% to about 15% 3-O-acetyl-11-keto-β-boswellic acid. Suitable extracts are commercially available, such as WokVel™ Boswellia powdered extract by Pharmanza India, which includes about 64% total boswellic acids and about 6.2% 3-O-acetyl-11-keto-β-boswellic acid, and Renaissance Boswellia extract, which includes about 63% total boswellic acids and about 10.5% 3-O-acetyl-11-keto-β-boswellic acid.

In an exemplary embodiment of the Asteridae extract and boswellic acid composition, the Asteridae extract is an OSSC Asteridae extract, for example a freeze-dried about 9:1 ethanol extract of *Carthamus tinctorious* that includes about 15% cornstarch, such that the effective plant:extract ratio is about 7.5:1, and a *Boswellia serrata* extract including about 60–70% total boswellic acid and about 6–10% 3-O-acetyl-11-keto-β-boswellic acid. The *Carthamus tinctorious* extract in this exemplary embodiment is about 10–20% of the composition and the *Bosswellia serrata* extract is about 85–95% of the composition (by weight), for example, such that the *Carthamus tinctorious* to *Bosswellia serrata* ratio is about 1.5:10 (about 13 % *Carthamus tinctorious* extract and about 87% *Bosswellia serrata* extract).

Asteridae extract and boswellic acid compositions are effective to selectively inihibit COX-2 and/or enhance COX-1 activity and to inhibit LO. In some cases Asteridae extract/boswellic acid compositions are effective to selectively inhibit 50% or more of COX-2 activity, such as 70% or 80% or more of COX-2 activity, for example 90% of more of COX-2 activity and to inhibit 50% or more of LO activity, such as 70% or 80% or more of LO activity, for example 90% of more of LO activity. In some cases, such Asteridae extract/boswellic acid compositions also either do not inhibit COX-1 activity or are effective to enhance COX-1 activity, such as enhancing COX-1 activity by about 1–300%, such as about 1–150% for example about 1–50% or 1–15%.

The exact proportions of the Asteridae extracts and boswellic acid used in the disclosed therapeutic agent compositions will depend on the concentration of active ingredients in each component. Using the guidance disclosed herein and a basic knowledge of drug preparation and pharmacology, one skilled in the art could easily adjust the proportions of the separate components of the composition so as to obtain a composition which has the therapeutic effects discussed herein.

In some cases the disclosed therapeutic agents are in the form of a pharmaceutical composition including Asteridae extract and optionally boswellic acid. For example the Asteridae extract and optionally boswellic acid in some cases is mixed with a pharmaceutical carrier (conventional tableting ingredients such as corn starch, lactose, sucrose, sorbitol, talc, stearic acid, magnesium stearate, dicalcium phosphate or gums) and/or other pharmaceutical diluents, such as water, to form a solid preformulation composition containing a substantially homogenous mixture of the therapeutic agent, or a non-toxic pharmaceutically acceptable salt thereof. When referring to the preformulation compositions as substantially homogenous, it is meant that the active ingredients are dispersed evenly throughout the composition so that the composition may readily be subdivided into equally effective unit dosage forms such as capsules, pills, and tablets.

In certain cases the pharmacuetical composition including Asteridae extract and optionally boswellic acid is a liquid preparation, such as a solution, syrup, or suspension. Such a liquid preparation is prepared by conventional means with pharmaceutically acceptable additives such as suspending agents (sorbitol syrup, methyl cellulose, or hydrogenated edible fats), emulsifying agents (lecithin or acacia), non-aqueous vehicles (almond oil, oily esters, or ethyl alcohol), preservatives (methyl or propyl p-hydroxybenzoates or sorbic acid), and artificial or natural colors and/or sweeteners.

In still other cases the pharmacuetical composition including Asteridae extract and optionally boswellic acid is formulated for topical administration, for example, as a lotion, ointment, gel, cream, suppository, drop, liquid, spray, or powder. In particular cases conventional pharmaceutical carriers, such as sterile aqueous solutions, powders, oily bases, thickeners and the like are used.

In some cases the pharmacuetical composition including Asteridae extract and optionally boswellic acid disclosed herein is formulated for parenteral administration, such as by combination with sterile aqueous solutions, which may also contain buffers, diluents and other suitable additives. In particular examples, the active ingredients are formulated for parenteral administration by injection, which includes using conventional catheterization techniques or infusion. The pharmaceutical composition can take such forms as a suspension, solution, or emulsion in oily or aqueous vehicles, and may contain formulating agents such as stabilizing, suspending, or dispersing agents. Alternatively, the active ingredients can be in powder form for reconstitution with a suitable vehicle, such as sterile pyrogert-free water, before use.

In some cases the disclosed therapeutic agent in the form of a pharmaceutical composition is combined with a physiologically acceptable oral vehicle into unit dosages. A unit dosage is a therapeutically effective amount of Asteridae extract and optionally boswellic acid for an administration period. In certain cases the administration period is a day and the unit dosage is given daily. In other cases the administration period is a week and the unit dosage is given weekly. In still other cases the unit dosage is formulated into smaller quantities of the extract or composition to provide for multiple doses in a day. A unit dosage will depend upon many factors including age, size, and condition of the subject being treated, the amount of the active ingredients (crude v. purified extract) and the frequency at which the unit dosage is administered. In particular cases the unit dosage is sufficient to achieve in vivo concentrations, for example systemic concentrations or concentrations at the site where a therapeutic effect is needed, of about 0.1 µg/ml or more of Asteridae extract, for example from about 0.1 µg/ml to about 50 µg/ml, and optionally about 1 µg/ml or more of boswellic acid, for example about 1 µg/ml to about 100 µg/ml (for example about 1.5 µg/ml to about 150 µg/ml of *Bosswellia serrata* extract including about 64% boswellic acid). In any event, the unit dosage is that which is physiologically acceptable to a subject.

In particular instances the unit dosage is from about 1 milligram (mg) to about 5000 mg. In some cases, the amount of the crude Asteridae extract in each unit dosage is from about 0.1 mg to about 300 mg (for example, about 100 to 200 mg) optionally with about 500 mg to about 1000 mg of boswellic acid (for example about 750 mg to about 1550 mg of *Bosswellia serrata* extract including about 64% boswellic acid, such as about 800–1200 mg of *Bosswellia serrata* extract including about 64% boswellic acid). In specific cases a unit dosage of the therapeutic agent includes about 150 mg of freeze-dried about 9:1 ethanol extract of *Carthamus tinctorious* that includes about 15% cornstarch, such that the effective plant:extract ratio is about 7.5:1 and about 1000 mg of *Bosswellia serrata* extract that includes about 64% boswellic acid. Lesser amounts of extract can be used if the extract is purified.

Methods of Using the Disclosed Therapeutic Agents and Combinations of Asteridae Extract and Boswellic Acid The therapeutic agents disclosed herein and combinations of Asteridae extract and boswellic acid are administered in a variety of ways, including orally, such as in a pharmaceutical carrier, for example a tablet, or in a subject's food or drink, topically, including ophthalmicly, vaginally, rectally, intranasally, and the like, and parenterally, for example, by intravenous drip or by intraperitoneal, subcutaneous, or intramuscular injection.

Asteridae extract is administered to a subject to selectively inhibit COX-2 and/or to enhance COX-1 activity or counter COX-1 inhibition by other compounds, such as COX-1 inhibiting NSAIDs. For example an OSSC Asteridae extract is administered in some cases to selectively inhibit COX-2 activity. In other cases an OSSC Asteridae extract is administered to enhance COX-1 activity. In still other cases an OSSC Asteridae extract is administered to selectively inhibit COX-2 activity and concomitantly enhance COX-1 activity. In other examples a water Asteridae extract is administered to enhance COX-1 activity or counter COX-1 inhibition caused by another compound, such as an NSAID. In still other cases an Asteridae extract including an OSSC and a water Asteridae extract is administered to selectively inhibit COX-2 and enhance COX-1.

Administration of Asteridae extract includes administering sufficient extract to achieve a therapeutically effective amount in a target tissue. For example, the dose achieves an in vivo target tissue concentration of about 0.1 µg/ml or more, such as about 0.1 to about 50 μg/ml of Asteridae extract, for example from about 3 μg/ml to about 50 μg/ml. In particular cases an OSSC Asteridae extract, such as an extract of *Carthamus tinctorious*, for example a freeze-dried about 9:1 ethanol extract of *Carthamus tinctorious* that includes about 15% cornstarch, such that the effective plant: extract ratio is about 7.5:1, is administered to achive an in vivo concentration of about 3–10 μg/ml. In other cases a water Asteridae extract, such as the water fraction of an ethanol Asteridae extract is administered to achieve an in vivo concentration of about 10–50 μg/ml.

Administration of Asteridae extract in the ranges discussed in the paragraph above inhibits COX-2 in a dose dependent fashion from about 10% to about 100% in certain cases, such as about 50% or more, about 70% or more, about 80% or more, or about 90% or more. For example, a 6.5:1 methanol extract at a concentration of about 0.3 μg/ml inhibited about 8% COX-2 activity and at a concentration of about 3 μg/ml inhibited about 92% COX-2 activity, as shown in FIG. 2. In another example, a freeze-dried dried about 9:1 ethanol extract of *Carthamus tinctorious* that included about 15% cornstarch, such that the effective plant:extract ratio was about 7.5:1 inhibited about 77% of COX-2 activity at a concentration of about 3 μg/ml. A methanol extracted fraction of the freeze-dried about 9:1 ethanol extract of *Carthamus tinctorious* that included about 15% cornstarch inhibited about 98% of COX-2 activity at a concentration of about 3 μg/ml.

COX-2 inhibition from administration of Asteridae extract in the ranges discussed above is selective. In particular, in some cases, administration of Asteridae extract in the ranges discussed above does not inhibit COX-1 activity to any significant degree. For example, a freeze-dried about 9:1 ethanol extract of *Carthamus tinctorious* that included about 15% cornstarch, such that the effective plant:extract ratio was about 7.5:1, did not inhibit COX-1 activity at a concentration of about 3 μg/ml (while inhibiting about 77% COX-2 activity). In other cases, administration of Asteridae extract enhances COX-1 activity. In specific cases, Asteridae extract is administered to enhance COX-1 activity in a dose dependent fashion from about 1% to about 300%. For example, the freeze-dried about 9:1 ethanol extract of *Carthamus tinctorious* discussed in this paragraph enhanced COX-1 activity by about 7% at 10 μg/ml. A 6.5:1 methanol extract at a concentration of about 3 μg/ml enhanced COX-1 activity by about 7% and at a concentration of about 50 μg/ml enhanced COX-1 activity by about 115% (while inhibiting about 92% COX-2 activity at 3 μg/ml) as shown in FIG. 3. In another example a 3:1 crude extract of *Carthamus tinctorious* enhanced COX-1 by about 1% at 10 μg/ml. Further, a water fraction of a freeze-dried 9:1 ethanol extract that included about 50% cornstarch, such that the effective plant:extract ratio was about 4.5:1, enhanced COX-1 activity by about 3% at 10 μg/ml.

In some cases a combination of Asteridae extract and boswellic acid is administered to a subject to selectively inhibit COX-2 activity, inhibit LO activity, and/or enhance COX-1 activity. Combined administration includes sequential and simultaneous administration. In sequential administration the Asteridae extract and boswellic acid are administered in any order so long as one component remains in the subject at the time of administration of the other component. For example, in some cases Asteridae extract is administered to the subject, such a in a tablet, and several hours later boswellic acid is administered to the subject, such as in a tablet. In other cases the Asteridae extract and boswellic acid are administered simultaneously, for example as components of a composition that includes Asteridae extract and boswellic acid such as is described above.

Administration of Asteridae extract as part of the disclosed combination includes administering sufficient Asteridae extract to achieve the therapeutically effective amount in a target tissue as discussed above for administration of Asteridae extract. The Asteridae extract includes any Asteridae extract as disclosed above. In particular cases the Asteridae extract is an OSSC Asteridae extract, a water Asteridae extract, or mixtures thereof. In some cases the Asteridae extract is an extract extracted at or below about 60° C.

Administration of boswellic acid as part of the disclosed combination includes administering sufficient boswellic acid to achieve a therapeutically effective amount in a target tissue. For example, the dose achieves an in vivo target tissue concentration of of about 1 μg/ml to about 100 μg/ml of boswellic acid. The boswellic acid includes the boswellic acid included in the Asteridae extract/boswellic acid therapeutic agent composition described. In particular cases the boswellic acid is , β-boswellic acid, such as 3-O-acetyl-11-keto-β-boswellic acid. In some cases the boswellic acid administered is a Burseracea extract, such as *boswellia serrata* extract. In specific cases *Boswellia serrata* extract including about 64% boswellic acid, such as WokVel™ Boswellia powdered extract, is administered in a sufficient amount to achieve a concentration of about 1.5 μg/ml to about 150 μg/ml of *boswellia* extract in vivo.

Administration of a combination of Asteridae extract and boswellic acid in the ranges discussed above inhibits COX-2 in a dose dependent fashion from about 10% to about 100% in certain cases, such as about 50% or more, about 70% or more, or about 90% or more. For example, a combination of freeze-dried about 9:1 ethanol extract of *Carthamus tinctorious* that included about 15% cornstarch, such that the effective plant:extract ratio was about 7.5:1, at a concentration of about 3 μg/ml and *Boswellia serrata* extract including about 64% boswellic acid at a concentration of about 15 μg/ml inhibited about 93% of COX-2 activity.

COX-2 inhibition from administration of the combination of Asteridae extract and boswellic acid is selective. In some cases, administration of the combination does not inhibit COX-1 activity to any significant degree. In other cases, administration of the combination enhances COX-1 activity. In specific cases, the combination is administered to enhance COX-1 activity in a dose dependent fashion from about 1% to about 300%, such as about 1–100%, for example 1–50% or 1–10%. For example, an OSSC Asteridae extract, such as an ethanol extract at about 10 μg/ml, in combination with boswellic acid, such as a *boswellia serrata* extract having about 60–70% total boswellic acid at about 15 μg/ml enhances COX-1 by about 1–10%. In another example, a water Asteridae extract, such as water fraction of an ethanol extract at about 10 μg/ml, in combination with boswellic acid, such as a *boswellia serrata* extract having about 60–70% total boswellic acid at about 15 μg/ml enhances COX-1 by about 1–5%.

Administration of the combination of Asteridae extract and boswellic acid in the ranges discussed above also inhibits LO activity, such as 5-LO activity, in a dose dependent fashion from about 10% to about 100% in certain cases. For example, a combination of freeze-dried about 9:1 ethanol extract of *Carthamus tinctorious* that included about 15% cornstarch, such that the effective plant:extract ratio was about 7.5:1, at a concentration of about 3 μg/ml and

*Bosswellia serrata* extract including about 64% boswellic acid at a concentration of about 15 µg/ml inhibited about 88% of LO activity.

In particular cases, administration of the combination of Asteridae extract and boswellic acid inhibits COX-2 to a greater extent that than administration of Asteridae extract alone at the same concentration as the Asteridae extract concentration in the combination. For example, a combination of freeze-dried about 9:1 ethanol extract of *Carthamus tinctorious* that included about 15% cornstarch, such that the effective plant:extract ratio was about 7.5:1, at a concentration of about 3 µg/ml and *Boswellia serrata* extract including about 64% boswellic acid at a concentration of about 20 µg/ml inhibited COX-2 about 20% more than the same *Carthamus tinctorious* extract alone inhibited COX-2 activity at about the same concentration, as shown in FIG. 4.

In particular cases, administration of the combination of Asteridae extract and boswellic acid inhibits LO to a greater extent that than administration of boswellic acid alone at the same concentration as the boswellic acid concentration in the combination. For example, a combination of freeze-dried about 9:1 ethanol extract of *Carthamus tinctorious* that included about 15% cornstarch, such that the effective plant:extract ratio was about 7.5:1, at a concentration of about 3 µg/ml and *Bosswellia serrata* extract including about 64% boswellic acid at a concentration of about 17 µg/ml inhibited LO about 100% more than the same *Bosswellia serrata* extract alone inhibited LO activity at about the same concentration, as shown in FIG. 5.

In some cases the Asteridae extract and/or combinations of the Asteridae extract and boswellic acid disclosed herein are administered to a subject to treat a COX-2/LO mediated condition. Examples of COX-2/LO mediated conditions include pain, headache, muscle ache, reperfusion injury to an ischemic organ, for example, reperfusion injury to the ischemic myocardium, myocardial infarction, inflammatory bowel disease, rheumatoid arthritis, osteoarthritis, hypertension, psoriasis, organ transplant rejections, organ preservation, impotence, radiation-induced injury, asthma, atherosclerosis, thrombosis, platelet aggregation, cancers, for example, colon, oral, blood, and skin cancer, influenza, stroke, burns, trauma, acute pancreatitis, pyelonephritis, hepatitis, autoimmune diseases, insulin-dependent diabetes mellitus, disseminated intravascular coagulation, fatty embolism, Alzheimer's disease, and adult and infantile respiratory diseases. In some cases a subject having a COX-2/LO mediated condition is selected for administration the Asteridae extract and/or combinations of the Asteridae extract and boswellic acid. Such selection can be made, for example, by diagnosing a subject with a COX-2/LO mediated condition.

In particular cases the Asteridae extract and/or combinations of the Asteridae extract and boswellic acid disclosed herein are administered to a subject to treat a COX-2/LO mediated condition in a subject having a condition for which COX-1 inhibition is disadvantageous, such as a condition for which COX-1 inhibition is contraindicated. Examples of conditions for which COX-1 inhibition is disadvantageous include, for example, gastric mucosal disorders, such as gastrointestinal bleeding, peptic ulcers, gastritis, regional enteritis, ulcerative colitis, diverticulitis or a recurrent history of gastrointestinal lesions; coagulation disorders, such as hypoprothrombinemia, thrombocytopenia, idiopathic thrombocytopenic purpura (ITP), hemophilia, or other bleeding problems; lupus; blood cancer; anemia; kidney and GI stress, such as from extensive physical activity, kidney transplantation, heat or cold attack, or surgery; liver dysfunctions, such as cirrhosis; and allergy. In certain instances such a subject is selected for administration of the Asteridae extract and/or combinations of the Asteridae extract and boswellic acid. The subject could be selected, for example, by making a diagnosis of a COX-2/LO mediated condition and any condition for which COX-1 inhibition is disadvantageous.

Additionally, the Asteridae extract and/or combinations of the Asteridae extract and boswellic acid disclosed herein are administered to a subject to treat disorders that would respond favorably to enhancement of COX-1, such as any of the conditions for which COX-1 inhibition is disadvantageous.

In other cases the Asteridae extract and/or combinations of the Asteridae extract and boswellic acid disclosed herein are administered prophalactically to treat a COX-2/LO mediated condition and/or a condition that would respond favorably to an increase in COX-1 activity to a subject at demonstrated risk for such a condition or conditions. The Asteridae extract and/or combinations of the Asteridae extract and boswellic acid is administered to prevent or inhibit the condition(s) or prevent, inhibit, or reduce the injury caused by the condition(s). In particular cases the Asteridae extract and/or combination of the Asteridae extract and boswellic acid is administered prophylactically to a subject at demonstrated risk for conditions associated with gastrointestinal mucosal disorders and injuries, such as gastritis, gastrointestinal bleeding, cirrhosis of the liver, gastrointestinal performation and gastrointestinal ulcers. Administration is prior to the onset of the gastrointestinal mucosal disorder or injury. This refers only to the onset of each instance of a gastrointestinal mucosal disorder or injury and would not preclude performance of the method with subjects who have had prior gastrointestinal mucosal disorders or injuries, that is, the methods disclosed herein also contemplate administration of the Asteridae extract and/or combination of the Asteridae extract and boswellic acid disclosed herein to a subject who has had a gastrointestinal mucosal disorder or injury in the past. Risk factors for gastric mucosal injury include NSAID use, *Helicobacter pylori* infection, chronic gastritis, a history of gastric ulcers, high stress, smoking, significant alcohol use, and/or increasing age. In some cases, these risks are determined by eliciting a subject's medical history. One of skill ordinary skill in the art would be able to determine these and other risk factors for gastrointestinal mucosal disorders and injury. In particular cases the Asteridae extract is administered to to a subject in combination with a COX-1 inhibiting NSAID, such as, for example, ibuprofen, acetaminophen, or aspirin, to enhance COX-1 activity and/or counter COX-1 inhibition by the NSAID.

In still other cases, Asteridae extract and/or the combination of Asteridae extract and boswellic acid disclosed herein is administered to a subject to treat kidney failure, such as acute renal failure or chronic renal failure. In particular cases the Asteridae extract and/or combination of the Asteridae extract and boswellic acid is administered prophylactically to a person at demonstrated risk for chronic kidney failure to inhibit kidney failure or reduce the accompanying injury. Risk factors for chronic kidney failure include diabetes mellitus, hypertension, various forms of nephritis, polycystic kidney disease, and use of NSAIDs. One of skill ordinary skill in the art would be able to determine these and other risk factors for kidney failure.

The following are merely examples of particular embodiments of the disclosed therapeutic agents and methods and are not intended to be limiting in any way.

EXAMPLE 1

This example demonstrates the significant, selective COX-2 inhibition and COX-1 enhancement caused by an Asteridae extract, specifically an extract of *Carthamus tinctorius*. In particular, as can be seen from the data discussed below, the Asteridae extract did not inhibit COX-1 activity and the COX-2/COX-1 $IC_{50}$ ratio for the Asteridae extract was 0.0. Thus, the extracts and compositions described herein are much more COX-2 selective than common NSAIDs.

About one hundred grams (g) of whole *Carthamus tinctorius* flower petals were placed into about 800 milliliters (mL) of methanol at room temperature. In other examples the flower petals were powdered, but no effect on the results were observed. This mixture was allowed to soak overnight. After evaporating the methanol, about 1 5.3 g of crude extract was obtained resulting in an extract ratio of 6.5:1. The extract was tested for COX-2 inhibition and COX-1 enhancement with COX-2 and COX-1 enzyme activity assays. COX-2 inhibition was assessed using COX-2 (human recombinant) isolated from Sf9 insect cells. The extract was pre-incubated with 1% dimethyl sulfoxide (DMSO), about 1 mM hematin, and about 500 µM phenol at 37° C. for 15 minutes. The reaction was initiated by the addition of 0.3 µM arachidonic acid as the substrate in a buffer of 100 milliMolar (mM) tris(hydroxymethyl)aminomethane Hydrochloride (Tris-HCI) at pH 7.7 and terminated after 5 minutes incubation at 37° C. After centrifugation, substrate conversion to $PGE_2$ was measured using an Amersham enzyme immunoassay (EIA) kit.

COX-1 enhancement was assessed using COX-1 isolated from human platelets. The extract was pre-incubated with 1% dimethyl sulfoxide (DMSO), at 37° C. for about 15 minutes. The reaction was initiated by the addition of about 50,000,000 cell endogenous arachidonic acid as the substrate in a buffer of 100 mM hepes at pH 7.4 and terminated after 15 minutes incubation at 37° C. After centrifugation, substrate conversion to $PGE_2$ was measured using an Amersham EIA kit.

With reference to FIG. 2, the results from the COX-2 EIA illustrates that the extract caused dose-dependent COX-2 inhibition. At concentrations of 0.003 µg/mL, 0.03 µg/mL, 0.3 µg/mL, and 3 µg/mL of extract, the percentages of COX-2 inhibition were about 4%, 8%, 40%, and 92%, respectively. The COX-2 $IC_{50}$ for the extract was about 0.411 µg/mL.

With reference to FIG. 3, the results from the COX-1 EIA illustrates that the extract, instead of inhibiting COX-1 activity like most selective COX-2 inhibitors, actually increased COX-1 activity at the reported concentrations. At concentrations of about 3 µg/mL and 50 µg/mL of extract, the percentages of increased COX-1 activity were about 7% and 115%, respectively. Thus, there was no COX-1 $IC_{50}$, so the COX-2/COX-1 $IC_{50}$ ratio was zero.

EXAMPLE 2

This example demonstrates COX-2 inhibition caused by other Asteridae extracts.

General procedure for making the extracts in this example:

About one hundred grams of whole *Carthamus tinctorius* flower petals is placed into 1000 ml of solvent at room temperature (about 1 8–25° C.). This mixture is allowed to soak overnight. The mixture is filtered to separate the solvent from the plant material. The plant material separated is placed in another 1000 ml of solvent at room temperature and this mixture is soaked for about 6 hours. This mixture is filtered into the solvent filtered from the first extraction. The solvent is then evaporated at a temperature of about 35–45° C. to obtain an extract. COX-2 and COX-1 activity are determined as described in Example 1.

1. Ethanol Extract

The general procedure was followed with ethanol as a solvent. A 9:1 ethanol extract was obtained. This extract caused an about 88% COX-2 inhibition at about about 3 µg/ml.

2. 70% Ethanol/30% Water Extract

The general procedure was followed with a mixture of 70% ethanol/30% water extract as the solvent. A 6.5:1 extract was obtained. This extract caused an about 52% COX-2 inhibition at about 3 µg/ml.

3. Hot Ethanol Extract

The general procedure was followed with ethanol as a solvent, but the ethanol was heated to about 65° C. and the mixture was maintained at this temperature during extraction. A 4.5:1 extract was obtained. This extract caused an about 27% COX-2 inhibition at about 3 µg/ml. The diminished COX-2 inhibition of this extract relative to the extract in 1, above, suggests that heating Asteridae extracts is detrimental to the ability of the extracts to inhibit COX-2. Thus, in some embodiments of the disclosed Asteridae extracts and methods of using them, exposure of the extracts to heat is avoided.

4. Spray Dried Ethanol Extract

The general procedure was followed with a mixture of 70% ethanol/30% water extract as the solvent. Then the extract was spray dried to obtain a powdered extract. Spray drying included diluting the extract with water to form a suspension of the extract in water, such as about 30% water (by weight), and spraying the suspension from a sprayer into a dryer in which the extract spray is opposed by forced air having a temperature of about 80° C. A powdered 6.5:1 extract was collected in the dryer. This extract caused an about 13% COX-2 inhibition at about 3 µg/ml. The diminished COX-2 inhibition of this extract relative to the extract in 2, above, reinforces the suggestion that heating Asteridae extracts is detrimental to the ability of the extracts to inhibit COX-2.

5. Freeze-Dried Ethanol Extract

The general procedure was followed with ethanol as a solvent. A 9:1 ethanol extract was obtained. To this extract cornstarch was added to form a 50% extract 50% cornstarch mixture. This mixture was freeze-dried at −50° C. A powdered extract was obtained with an effective plant:extract ratio of about 4.5:1. This extract caused an about 48% COX-2 inhibition at about 3 µg/ml.

6. Ethyl Acetate Fraction of the Freeze-Dried Ethanol Extract in 5, above

The freeze-dried ethanol extract in 5, above, was suspended in water and fractioned three times by solvent/solvent partitioning with equal volumes of water-saturated ethyl acetate. The ethyl acetate layers from each fractionation were combined, evaporated to obtain an extract, and freeze-dried at about −50° C. This ethyl acetate extract caused an about 85% COX-2 inhibition at about 3 µg/ml.

7. Freeze-Dried Ethanol Extract

The general procedure was followed with ethanol as a solvent. A 9:1 ethanol extract was obtained. Cornstarch was added to this extract form a 85% extract 15% cornstarch mixture with an effective plant:extract ratio of about 7.5:1. This mixture was freeze-dried at −50° C. The freeze-dried extract was powdered. This powdered extract caused an about 77% COX-2 inhibition and an about 4% COX-1 enhancement at about 3 µg/ml.

EXAMPLE 3

This example demonstrates that water extraction of a plant from the Asteridae sub-family does not produce extracts exhibiting COX-2 inhibition, but does produce extracts exhibiting COX-1 enhancement.

1. Water Extract

The general procedure from Example 2 was followed with a water as a solvent. A 3:1 extract was obtained. This extract did not inhibit COX-2 activity, but enhanced COX-1 activity by about 1% at about 101 µg/ml.

2. Water Fraction of a Freeze-Dried Ethanol Extract

The water layers of the freeze-dried ethanol extract (extract 5 of Example 2) that were obtained in producing the ethyl acetate fraction above (extract 6 of Example 2) were combined, evaporated to obtain an extract, and freeze-dried at about −50° C. This extract did not inhibit COX-2 activity at 3 µg/ml, and caused a 3% enhancement of COX-1 activity at about 10 µg/ml.

EXAMPLE 4

This example demonstrates the COX-2 inhibiting effect of fractions of an OSSC Asteridae extract.

A freeze-dried ethanol extract (extract 7 of Example 2) was fractioned by column chromatography using various eluents sequentially. About 1200 mg of the freeze-dried ethanol extract was suspended in about 3 ml of water and loaded onto a 10×2.5 cm column packed with about 20 g HP-20 and pre-equilibrated with about 200 ml of a 15% acetonitrile/80% water solution. The freeze-dried ethanol extract was then fractioned with about 100 ml (about 2× the column volume) of eluent 1 (see Table), which was collected. The other listed eluents were run through the column in sequence and collected. The collected eluents were evaporated at about 35–45° C. and freeze-dried at about −50° C. Bioassays of the extracts obtained from each eluent for COX-2 activity was performed as described in Example 1.

TABLE 1

| Fraction | Eluent | Yield | Approximate Cox-2 inhibition at a concentration of 3 µg/ml |
|---|---|---|---|
| Original extract | NA | NA | 77% |
| 1 | 15% ACN/85% Water | 577 mg | −1% |
| 2 | 30% ACN/70% Water | 155 mg | 3% |
| 3 | 45% ACN/55% Water | 98 mg | 11% |
| 4 | 60% ACN/40% Water | 64 mg | 71% |
| 5 | 75% ACN/25% Water | 37 mg | 87% |
| 6 | Methanol | 38 mg | 98% |
| 7 | Acetone | 132 mg | 91% |

As can be seen in Table 1, the greater the proportion of organic compounds in the organic solvent, the more pronounced the COX-2 inhibition of the resulting Asteridae extract. Additionally, these data indicate that alcohol, such as methanol, and acetone are particularly effective solvents for producing COX-2 inhibitory Asteridae extracts.

EXAMPLE 5

This example demonstrates synergistic effects on COX-2 and 5-LO inhibition from a combination of Asteridae extract and boswellic acid.

Asteridae extract, specifically the freeze-dried, ethanol extracted, *Carthamus tinctorious* extract of Example 2 (extract 7), and boswellic acid, specifically WokVel™ *Boswellia*, a powdered *Boswellia serrata* extract having about 64% total boswellic acid and about 6% 3-O-acetyl-11-keto-β-boswellic acid were both tested for COX-2 and LO inhibition. In addition, a composition of both of these extracts was tested for COX-2 and LO inhibition. The composition was prepared by mixing 150 mg of the *Carthamus tinctorious* extract with 1000 mg of the *Bosswellia serrata* extract.

COX-2 Inhibition

COX-2 inhibition was determined as described in Example 1. The Asteridae extract inhibited about 77% of COX-2 activity at a concentration of about 3 µg/ml, as noted above in Example 2 and as illustrated in FIG. 4. The boswellic acid did not inhibit COX-2 at a concentration of about 15 µg/ml as can be seen in FIG. 4. Surprisingly, as shown in FIG. 4, the composition including the Asteridae extract and boswellic acid inhibited about 93% of COX-2 activity at a concentration of 24ug/ml (equivalent to about 3 ug/ml of the *Carthamus tinctorious* extract and about 20 µg/ml of the *Boswellia serrata* extract). This demonstrates that the combination of an OSSC Asteridae extract with boswellic acid can increase COX-2 inhibition by at least about 20% over the OSSC Asteridae extract alone. This effect cannot be due to an additive inhibition caused by boswellic acid since, as shown in FIG. 4, boswellic acid does not inhibit COX-2.

LO Inhibition

LO inhibition, specifically 5-LO inhibition, was determined. 5-LO inhibition was assessed using 5-LO (human recombinant) isolated from human peripheral blood mononuclear leukocytes (PBMN) cells. The Asteridae extract, boswellic acid, and combinations thereof, were pre-incubated with 1% dimethyl sulfoxide (DMSO) at 37° C. for 15 minutes. The reaction was initiated by the addition of endogenous arachidonic acid from PBMN cells as the substrate in a buffer of Hank's Balanced Salt Solution (HBSS) (0.44 mM potassium phosphate, 5.37 mM potassium chloride, 0.34 mM dibasic sodium phosphate, 136.89 mM sodium chloride, 5.5 mM D-glucose) at 37° C. and terminated after 15 minutes incubation. After centrifugation, substrate conversion to $LTB_4$ was measured using an Amersham enzyme immunoassay (EIA) kit.

The Asteridae extract did not inhibit 5-LO activity at a concentration of about 3 µg/ml, but rather enhanced 5-LO activity by about 4%, as shown in FIG. 5. As also is shown in FIG. 5, the boswellic acid inhibited about 42% of 5-LO activity at a concentration of 15 µg/ml. Suprisingly, the composition including the Asteridae extract and boswellic acid inhibited about 88% of 5-LO activity at a concentration of 20 µg/ml (equivalent to about 3 µg/ml of the *Carthamus tinctorious* extract and about 17 µg/ml of the *Boswellia serrata* extract) as illustrated in FIG. 5. This demonstrates that the composition can increase LO inhibition by at least about 100% over the boswellic acid alone. This effect cannot be due to an additive inhibition caused by the Asteridae extract since Asteridae extract does not inhibit LO.

The above-described examples merely disclose particular embodiments of the disclosed therapeutic agents and methods. They are not intended to be limiting in any way. Moreover, although the therapeutic agents and methods disclosed have been described herein in detail, it will be understood by those of skill in the art that variations may be made thereto without departing from the spirit of the invention or scope of the appended claims.

We claim:

1. A composition comprising:
   an extract of *Boswellia serrata*; and
   an organic solvent/supercritical (OSSC) extract of *Carthamus tinctorious*;
   wherein the ratio of extract of *Boswellia serrata* to OSSC extract of *Carthamus tinctorious* is 1000:150 and the concentration of extract of *Boswellia serrata* and OSSC extract of *Carthamus tinctorious* combined is 24 μg/ml.

2. The composition of claim 1, wherein the extract of *Boswellia serrata* comprises about 64% total boswellic acid.

3. The composition of claim 2, wherein the extract of *Boswellia serrata* comprises about 6% 3-O-acetyl-11-keto-β-boswellic acid.

4. The composition of claim 3, wherein the OSSC extract of *Carthamus tinctorious* is an alcohol extract of *Carthamus tinctorious*.

5. The composition of claim 4, wherein the alcohol extract is an ethanol extract.

6. The composition of claim 5, wherein the OSSC extract of *Carthamus tinctorious* was extracted from *Carthamus tinctorious* at about 45° C. or below.

7. The composition of claim 6, wherein the OSSC extract of *Carthamus tinctorious* is an extract from the flower of the *Carthamus tinctorious* plant.

8. The composition of claim 7, wherein the OSSC extract of *Carthamus tinctorious* has an effective plant to extract ratio of about 7.5:1.

9. The composition of claim 8, wherein the OSSC extract of *Carthamus tinctorious* is a freeze-dried, powdered extract.

10. A composition comprising:
    an extract of *Boswellia serrata*; and
    an OSSC extract of *Carthamus tinctorious*;
    wherein the ratio of extract of *Boswellia serrata* to OSSC extract of *Carthamus tinctorious* is 1000:150 and the concentration of extract of *Boswellia serrata* and OSSC extract of *Carthamus tinctorious* combined is 20 μg/ml.

11. The composition of claim 10, wherein the extract of *Boswellia serrata* comprises about 64% total boswellic acid.

12. The composition of claim 11, wherein the extract of *Boswellia serrata* comprises about 6% 3-O-acetyl-11-keto-β-boswellic acid.

13. The composition of claim 12, wherein the OSSC extract of *Carthamus tinctorious* is an alcohol extract of *Carthamus tinctorious*.

14. The composition of claim 13, wherein the alcohol extract is an ethanol extract.

15. The composition of claim 14, wherein the OSSC extract of *Carthamus tinctorious* was extracted from *Carthamus tinctorious* at about 45° C. or below.

16. The composition of claim 15, wherein the OSSC extract of *Carthamus tinctorious* is an extract from the flower of the *Carthamus tinctorious* plant.

17. The composition of claim 16, wherein the OSSC extract of *Carthamus tinctorious* has an effective plant to extract ratio of about 7.5:1.

18. The composition of claim 17, wherein the OSSC extract of *Carthamus tinctorious* is a freeze-dried, powdered extract.

19. A composition comprising:
    an extract of *Carthamus tinctorious* wherein the extract of *Carthamus tinctorious* is a freeze-dried, powdered, ethanol extract from a flower of the *Carthamus tinctorious* plant that was extracted at about 45° C. or below; and
    an extract of *Boswellia serrata* wherein the extract of *Boswellia serrata* comprises about 6% 3-O-acetyl-11-keto-β-boswellic acid and about 64% total boswellic acid;
    wherein the ratio of extract of *Boswellia serrata* to extract of *Carthamus tinctorious* is 1000:150 and the concentration of extract of *Boswellia serrata* and extract of *Carthamus tinctorious* combined is 24βg/ml.

20. A composition comprising:
    an extract of *Carthamus tinctorious* wherein the extract of *Carthamus tinctorious* is a freeze-dried, powdered, ethanol extract from a flower of the *Carthamus tinctorious* plant that was extracted at about 45° C. or below; and
    an extract of *Boswellia serrata* wherein the extract of *Boswellia serrata* comprises about 6% 3-O-acetyl-11-keto-β-boswellic acid and about 64% total boswellic acid;
    wherein the ratio of extract of *Boswellia serrata* to extract of *Carthamus tinctorious* is 1000:150 and the concentration of extract of *Boswellia serrata* and extract of *Carthamus tinctorious* combined is 20 μg/ml.

21. A composition comprising:
    an extract of *Carthamus tinctorious* wherein the extract of *Carthamus tinctorious* is prepared by mixing whole *Carthamus tinctorious* flower petals with ethanol, filtering the ethanol from the flower petals, evaporating the ethanol at a temperature of about 35° C. to about 45° C. to obtain a first extract, combining the first extract with cornstarch to form a mixture of 85% extract and 15% cornstarch, freeze-drying the mixture, and powdering the mixture to obtain the extract of *Carthamus tinctorious*; and
    an extract of *Boswellia serrata* comprising about 6% 3-O-acetyl-11-keto-β-boswellic acid and about 64% total boswellic acid;
    wherein the ratio of extract of *Boswellia serrata* to extract of *Carthamus tinctorious* is 1000:150 and the concentration of extract of *Boswellia serrata* and extract of *Carthamus tinctorious* combined is 24 pg/ml.

22. A composition comprising: an extract of *Carthamus tinctorious* wherein the extract of *Carthamus tinctorious* is prepared by mixing whole *Carthamus tinctorious* flower petals with ethanol, filtering the ethanol from the flower petals, evaporating the ethanol at a temperature of about 350° C. to about 450° C. to obtain a first extract, combining the first extract with cornstarch to form a mixture of 85% extract and 15% cornstarch, freeze-drying the mixture, and powdering the mixture to obtain the extract of *Carthamus tinctorious*; and
    an extract of *Boswellia serrata* comprising about 6% 3-O-acetyl-11-keto-β-boswellic acid and about 64% total boswellic acid;
    wherein the ratio of extract of *Boswellia serrata* to extract of *Carthamus tinctorious* is 1000:150 and the concentration of extract of *Boswellia serrata* and extract of *Carthamus tinctorious* combined is 20 μg/ml.

* * * * *